(12) United States Patent
Cho

(10) Patent No.: US 7,281,414 B2
(45) Date of Patent: Oct. 16, 2007

(54) APPARATUS, A METHOD, AND MEASURING SENSORS FOR SCANNING STATES OF ENGINE OIL

(75) Inventor: Jin Hee Cho, Suwon (KR)

(73) Assignee: Hyundai Motor Company, Seoul (KR)

( * ) Notice: Subject to any disclaimer, the term of this patent is extended or adjusted under 35 U.S.C. 154(b) by 0 days.

(21) Appl. No.: 11/291,871

(22) Filed: Nov. 30, 2005

(65) Prior Publication Data

US 2006/0114007 A1 Jun. 1, 2006

(30) Foreign Application Priority Data

Nov. 30, 2004 (KR) ............. 10-2004-0099177
Nov. 22, 2005 (KR) ............. 10-2005-0111791

(51) Int. Cl.
*G01N 11/10* (2006.01)
(52) U.S. Cl. ................................. 73/54.24; 73/10
(58) Field of Classification Search ............. 73/118.1, 73/54.24, 54.25, 54.26, 54.27
See application file for complete search history.

(56) References Cited

U.S. PATENT DOCUMENTS

| | | | |
|---|---|---|---|
| 2,518,348 A * | 8/1950 | Mason | 73/54.24 |
| 3,827,300 A * | 8/1974 | Thaler | 73/304 C |
| 4,302,965 A | 12/1981 | Johnson et al. | 73/54.07 |
| 4,947,689 A | 8/1990 | Hochstein | |
| 5,103,368 A * | 4/1992 | Hart | 361/284 |
| 5,571,952 A | 11/1996 | Kauzlarich | 73/54.24 |
| 5,750,887 A * | 5/1998 | Schricker | 73/117.3 |
| 5,831,154 A * | 11/1998 | Guertler et al. | 73/117.3 |
| 5,900,810 A * | 5/1999 | Park et al. | 340/450.3 |
| 5,929,754 A * | 7/1999 | Park et al. | 340/439 |
| 6,260,408 B1 * | 7/2001 | Vig et al. | 73/64.53 |
| 6,286,363 B1 * | 9/2001 | Discenzo | 73/53.01 |
| 6,327,900 B1 * | 12/2001 | Mc Donald et al. | 73/117.3 |
| 6,443,006 B1 * | 9/2002 | Degrave | 73/304 C |

(Continued)

FOREIGN PATENT DOCUMENTS

JP 60-013722 1/1985

(Continued)

OTHER PUBLICATIONS

Jeff Tyson, "How Flash Memory Works", Aug. 2000, http://electronics.howstuffworks.com/flash-memory.htm.*

(Continued)

*Primary Examiner*—Michael Cygan
(74) *Attorney, Agent, or Firm*—Morgan Lewis & Bockius LLP

(57) ABSTRACT

The present invention relates to an apparatus, a method, and a sensor for scanning engine oil of a vehicle. An apparatus for scanning engine oil according to an exemplary embodiment of the present invention includes an oil property measuring part for measuring physical and chemical properties of engine oil; a driving condition measuring part for measuring a engine driving condition; a control portion where predetermined values about conditions of engine oil according to engine driving conditions are stored as set values, for selecting a set value corresponding to a measured engine driving condition and calculating a result value about a quality of engine oil on the basis of comparison with a measured value determined according to an engine driving condition inputted from the driving condition measuring part and the set value; and an output part for outputting the result.

16 Claims, 11 Drawing Sheets

U.S. PATENT DOCUMENTS

| | | | |
|---|---|---|---|
| 6,449,538 B1 * | 9/2002 | Kubo et al. | 701/30 |
| 6,553,812 B2 * | 4/2003 | Park et al. | 73/54.01 |
| 6,681,172 B2 * | 1/2004 | Pfeiffer et al. | 701/113 |
| 2005/0241989 A1 * | 11/2005 | Sant et al. | 208/18 |
| 2005/0268884 A1 * | 12/2005 | Yokoyama | 123/299 |
| 2006/0218996 A1 * | 10/2006 | Matsiev et al. | 73/64.53 |

FOREIGN PATENT DOCUMENTS

| | | |
|---|---|---|
| JP | 03-077022 | 4/1991 |
| JP | 06-034423 | 2/1994 |
| JP | 06-123699 | 5/1994 |
| JP | 08-247917 | 9/1996 |
| JP | 2003-083935 | 3/2003 |
| JP | 2003-107026 | 4/2003 |
| JP | 2004-045287 | 2/2004 |
| KR | 1990-0012087 | 8/1990 |
| WO | WO 91/17421 | * 11/1991 |

OTHER PUBLICATIONS

Charles Kozierok, "Read-Only Memory", Apr. 2001, http://www.pcguide.com/ref/ram/typesROM-c.html.*

* cited by examiner

APPARATUS, A METHOD, AND MEASURING SENSORS FOR SCANNING STATES OF ENGINE OIL

CROSS-REFERENCE TO RELATED APPLICATION

This application claims priority to and the benefit of Korean Patent Application No. 10-2004-0099177 filed in the Korean Intellectual Property Office on Nov. 30, 2004, and Korean Patent Application No. 10-2005-0111791 filed in the Korean Intellectual Property Office on Nov. 22, 2005 the entire contents of which are incorporated herein by reference.

BACKGROUND OF THE INVENTION

1. (a) Field of the Invention

The present invention relates to an apparatus, a method, and a sensor for scanning states of engine oil of a vehicle. According to the exemplary embodiments of the present invention, physical properties, chemical properties, and a quantity of engine oil are measured by respective sensors or a complex sensor, and then the quality of engine oil is determined by comparing a measured value of properties of engine oil with a predetermined value according to driving conditions or driving history information, and is expressed on the instrument panel such that the driver can notice whether it can be further used. In addition, exchange history, consumed quantity, and information of oxidization history of the engine oil are provided to the system scanner.

2. (b) Description of the Related Art

Since engine oil may include various materials and additives, and may be made in various manufacturing processes, the engine oil may have physical and chemical diversities and its quality may be variously changed according to the degree of oxidation, the condition of the engine, the kind of fuel used, driving conditions, and environmental conditions. Therefore, an apparatus or a system for scanning and monitoring engine oil should accurately and efficiently measure diverse qualities of the engine oil, and should indicate current condition, refill timing, and exchange timing of the engine oil.

Generally, engine oil functions to reduce friction, to cool down the engine, to disperse weight, to seal, to clean, and to prevent rust. However, as the engine oil is used, the above-mentioned functions become less effective. Since engine oil is used under high temperature in the combustion chamber, engine oil becomes oxidized and materials generated by combustion are contained in the engine oil. In addition, fuel like gasoline or diesel leaking at the injector may dilute engine oil, and metal fragments due to abrasion of frictional parts of the engine may be precipitated or float in the engine oil. In addition, when a problem occurs in the engine, antifreeze solution or water can flow into the engine oil through a connecting part (for example a gasket) of the engine.

Generally, under normal conditions when there is no problem in the engine, as the age of the engine oil becomes longer, the viscosity of the engine oil increases. Therefore, during the driving, the increased viscosity of the engine oil may problematically create excessive friction loss.

However, in the case that fuel has leaked through the injector or water increases in the engine oil, as the engine is operated, the viscosity of the engine oil decreases. Then, excessive abrasion may occur at the frictional parts of the engine. Therefore, the viscosity is one of the important physical properties of engine oil and should be measured accurately.

Conventional apparatus for measuring physical properties of engine oil use a method for merely measuring electrical capacity of the coil installed in a sensor, or measuring electrical capacity by a sensor having a network structure made by semiconductor processing. Therefore, it is difficult to correctly measure the viscosity of the engine oil. It is also difficult to measure chemical properties of the engine oil by measuring electrical capacity and to secure durability of the sensor, because metal fragments contained in the engine oil become attached to the sensor.

A conventional method for measuring the level of engine oil is a manual method that uses the naked eye with an installed oil level gauge. However, such a method is very inconvenient, and it is impossible to measure oil level when driving.

Generally, a pressure drop warning lamp installed in an instrument panel is lit when the oil level is below an oil pump pickup tube. When the oil pressure is much lower than the general pressure of 5 atm, for example lower than 0.5 atm, the pressure drop warning lamp is operated. However, even if the driver stops operation of the engine as soon the pressure drop warning lamp is seen, the engine may have already incurred serious damage. Even if it is very short time, the frictional parts of the engine can be seriously damaged, and the damage cannot be reversed by refilling the engine oil. Therefore, it is important to provide an oil level sensor by which monitoring the level of engine oil is always possible.

The above information disclosed in this Background section is only for enhancement of understanding of the background of the invention and therefore it may contain information that does not form the prior art that is already known in this country to a person of ordinary skill in the art.

SUMMARY OF THE INVENTION

Embodiments of the present invention provide an apparatus, a method, and a sensor for scanning states of engine oil of a vehicle, having advantages of notifying accurately measured states of engine oil to the driver or engineer, and improving accuracy and durability. An exemplary apparatus for scanning states of engine oil according to an embodiment of the present invention includes an oil property measuring part for measuring physical and chemical properties of engine oil; a driving condition measuring part for measuring engine driving conditions; a control portion for storing conditions of engine oil corresponding to engine driving conditions as set values, for selecting a set value for a state of engine oil corresponding to the measured engine driving conditions, and for calculating a result value regarding a quality of engine oil on the basis of comparison of measured values for the state of engine oil inputted from the driving condition measuring part and the set value; and an output part for outputting predetermined output depending on the result value.

The output part may be an instrument panel or a system scanner.

The oil property measuring part includes at least one of an oil viscosity sensor, an oil level sensor, an oil temperature sensor, and an oil oxidation degree sensor.

The oil property measuring part is a complex sensor including an oil viscosity sensor, an oil level sensor, an oil temperature sensor, and an oil oxidation degree sensor.

An exemplary complex sensor may include a cylindrical case having a hollow space therein, the oil level sensor, the oil oxidation degree sensor, the oil viscosity sensor, and the oil temperature sensor installed in the case, and a DSP for calculating values for physical and chemical properties of engine oil on the basis of values measured by each of the sensors. The oil level sensor includes an input electrode having a shape of a pipe, installed in the case, and formed such that electric current can be applied thereto, and an oil level electrode having a shape of pipe, disposed apart from an inner surface of the input electrode, and formed to receive electric current from the input electrode. The oil oxidation degree sensor includes the input electrode, and an oil oxidation degree electrode having a shape of a pipe, disposed at a lower portion of the oil level electrode and formed to receive electric current applied from the input electrode. The oil viscosity sensor includes a piezoelectric element and a metal membrane covering the piezoelectric element, and the oil temperature sensor is mounted to the case.

The piezoelectric element of the oil viscosity sensor may have a self-cleaning function by vibrating engine oil when the electric current is applied thereto.

An oil hole through which the engine oil passes may be formed at the case and the input electrode.

The oil viscosity sensor may be mounted to the inside of the oil oxidation degree electrode with an O-ring made of rubber.

An exemplary DSP may include an input/output port for receiving information by communicating with the oil property measuring part, an ECU, and the output part, and outputting a control signal; a CPU for calculating a quality of engine oil on the basis of measured values inputted through the input/output port and information of the engine driving condition inputted from the ECU; a flash memory for storing history of the condition of engine oil calculated by the CPU in a sequence of time; and a ROM for storing a program for operating the CPU.

An exemplary oil level sensor may include an input electrode formed such that an electric current is applied thereto, and an oil level electrode disposed apart from the input electrode and formed to receive the electric current output from the input electrode. The control portion calculates a capacitance and a dielectric constant of engine oil between the input electrode and the oil level electrode on the basis of the input current of the input electrode and the output current of the oil level electrode, and calculates an oil level on the basis of the calculated capacitance and dielectric constant of engine oil.

The input electrode has a shape of a pipe, and the oil level electrode has a shape of a pipe having a smaller diameter than the input electrode.

The oil level electrode is divided into a plurality of parts, and the control portion calculates a plurality of oil levels at respective divided parts of the oil level electrode on the basis of signals of the output electric current of the oil level electrodes and the input electric current of the input electrode.

The apparatus for scanning states of engine oil may further comprise a supporting part for mounting the oil level electrode, wherein the supporting part is formed of an insulating material to have a shape of a pipe, and the oil level electrode is fixed to an exterior surface of the supporting part.

Four vertical protruded parts may be formed along a longitudinal direction on the outer surface of the supporting part, and they are disposed between two adjacent divided parts of the oil level electrode so as to insulate respective divided parts of the oil level electrode.

An exemplary oil oxidation degree sensor may comprise an input electrode for applying an electric current, and an oil oxidation degree electrode disposed apart from the input electrode and formed to receive the electric current from the input electrode. The control portion calculates a capacitance of engine oil between the input electrode and the oil oxidation degree electrode on the basis of the input electric current of the input electrode and the output electric current of the oil oxidation degree electrode, and calculates a dielectric constant on the basis of the calculated capacitance and calculates an oil level on the basis of the calculated capacitance and dielectric constant of engine oil.

The input electrode may have a shape of a pipe, and the oil oxidation degree electrode may have a shape of a pipe having a smaller diameter than the input electrode.

An exemplary oil viscosity sensor may include a viscosity sensor case, a pipe-shaped piezoelectric element, an inside electrode mounted to the inner surface of the piezoelectric element and vertically separated therefrom, an outside electrode mounted to the exterior surface of the piezoelectric element, and a plurality of electric wires for supplying electric power to an inside electrode. One part of the piezoelectric element with the outside electrode is exposed to the engine oil and the other part of the piezoelectric element with the outside electrode is exposed to air, and when an electric current is applied, the two parts of the piezoelectric element are torsionally vibrated in opposite directions to each other. The control portion calculates a relative viscosity of engine oil on the basis of a measured damping force of air and a measured damping force of engine oil.

The inner surface of the viscosity sensor case is projected inward, a longitudinal center of the outside electrode is fixedly mounted to the projected part of the inner surface of the viscosity sensor case, and the inside electrode is vertically separated therefrom at a position corresponding to a fixing position of the outside electrode and is fixed to the viscosity sensor case.

The piezoelectric element of the oil oxidation degree sensor may have a self-cleaning function by vibrating engine oil when the electric current is applied.

An exemplary oil viscosity sensor may include a viscosity sensor case including a vibration tube extended downward, a ring-shaped piezoelectric element disposed inside of the viscosity sensor case, rings disposed to contact an upper surface and an lower surface of the piezoelectric element, and a vibration shaft with a flywheel mounted to a middle part thereof and a probe mounted to a lower part thereof. The flywheel is fixed on the ring disposed on the piezoelectric element, the probe is mounted to the vibration tube, the probe and the vibration tube exposed in the engine oil are vibrated due to the vibration of the piezoelectric element, and the control portion calculates a viscosity of engine oil on the basis of the damping force of the engine oil generated by the vibration of the probe and the vibration tube.

A plurality of piezoelectric elements may be stacked, and a plurality of the rings are interposed between the piezoelectric elements.

The ring may be made of copper.

A method for scanning engine oil according to an exemplary embodiment of the present invention includes measuring at least one of physical properties of engine oil; measuring at least one of chemical properties of engine oil; measuring an engine driving condition; selecting a set value for an oil state corresponding to the current engine driving condition among stored set values corresponding to a predetermined engine driving condition by comparing measured values corresponding to physical and chemical properties of engine oil with the selected set value for the oil state; calculating a result value on the basis of the comparison; and outputting a predetermined output corresponding to the result through an output part.

The measuring at least one of the physical properties of engine oil may include at least one of measuring a viscosity of engine oil with an oil viscosity sensor, measuring a level of engine oil with an oil level sensor, measuring an amount of engine oil, and measuring a temperature of engine oil with a oil temperature sensor.

The measuring a chemical property may include measuring a dielectric constant of the engine oil with an oil oxidation degree sensor.

The measuring an engine driving condition includes at least one of measuring a vehicle speed with a vehicle speed sensor, measuring an amount of intake air with an air flow sensor, and measuring engine rotation speed with a crank angle sensor.

The method may further comprise storing the measured value and the result value in the flash memory.

The output part may be an instrument panel or a system scanner.

The predetermined set values about conditions of engine oil corresponding to the respective engine driving conditions may be amended on the basis of a history of engine operation.

The predetermined values may comprise a limit value of viscosity of engine oil, and the limit value of viscosity of engine oil is determined on the basis of at least one of an amount of change of engine oil temperature, an amount of change of engine rotation speed, an amount of change of engine driving mileage, an amount of change of intake air measured by the air flow sensor, and an amount of change of air in the idle state.

The predetermined values include a limit value of a degree of oxidation of engine oil, and the limit value of viscosity of engine oil is determined on the basis of at least one of an amount of change of engine oil temperature, an amount of change of engine rotation speed, an amount of change of engine mileage, an amount of change of intake air measured by the air flow sensor, and an amount of change of air in the idle state.

The measuring a viscosity of engine oil with an oil viscosity sensor includes vibrating a piezoelectric element, measuring a damping force of engine oil caused by a vibration of the piezoelectric element, and calculating viscosity of engine oil on the basis of the damping force.

The measuring a viscosity of engine oil with an oil viscosity sensor may include vibrating a piezoelectric element, measuring a damping force of engine oil caused by a vibration of the piezoelectric element, measuring a damping force of air caused by a vibration of the piezoelectric element, and calculating a relative viscosity of engine oil on the basis of the measured damping force of engine oil and the measured damping force of air.

An oil level sensor according to an exemplary embodiment of the present invention may include an input electrode formed such that electric current is applied thereto, and an oil level electrode disposed apart from the input electrode and formed to receive the electric current output from the input electrode, and the control portion calculates a capacitance and a dielectric constant of engine oil between the input electrode and the oil level electrode on the basis of the input current of the input electrode and the output current of the oil level electrode, and calculates an oil level on the basis of the calculated capacitance and dielectric constant of engine oil.

The input electrode may have a shape of a pipe, and the oil level electrode has a shape of a pipe having a smaller diameter than the input electrode.

The oil level electrode may be divided into a plurality of parts, and the control portion calculates a plurality of oil levels at the respective divided parts of oil level electrode on the basis of signals of the output electric current of the oil level electrodes and the input electric current of the input electrode.

The oil level sensor may further include a supporting part for mounting the oil level electrode, wherein the supporting part is formed of an insulating material to have a shape of a pipe, and the oil level electrode is fixed to an exterior surface of the supporting part.

Four vertical protruded parts may be formed along a longitudinal direction on outer surface of the supporting part, and the vertical protruded parts are disposed between two adjacent divided parts of the divided oil level electrode so as to insulate respective divided parts of the divided oil level electrodes.

An oil oxidation degree sensor according to an exemplary embodiment of the present invention includes an input electrode applying electric current, and an oil oxidation degree electrode disposed apart from the input electrode and formed to receive the electric current the from the input electrode. The control portion calculates a capacitance of engine oil between the input electrode and the oil oxidation degree electrode on the basis of the input electric current of the input electrode and the output electric current of the oil oxidation degree electrode, calculates a dielectric constant on the basis of the calculated capacitance, and calculates an oil level on the basis of the calculated capacitance and dielectric constant of engine oil.

The input electrode may have a shape of a pipe, and the oil oxidation degree electrode has a shape of a pipe having a smaller diameter than the input electrode.

An oil viscosity sensor according to an exemplary embodiment of the present invention includes a viscosity sensor case, a pipe-shaped piezoelectric element, an inside electrode mounted to the inner surface of the piezoelectric element and vertically separated therefrom, an outside electrode mounted to the exterior surface of the piezoelectric element, and a plurality of electric wires for supplying electric power to an inside electrode. One part of the piezoelectric element with the outside electrode is exposed to the engine oil and the other part of the piezoelectric element with the outside electrode is exposed to air, and when an electric current is applied, the two parts of the piezoelectric element are torsionally vibrated in opposite directions to each other, the control portion calculates a relative viscosity of engine oil on the basis of a measured damping force of air and a measured damping force of engine oil.

A inner surface of the viscosity sensor case may be projected inward, a longitudinal center of the outside electrode is fixedly mounted to the projected part of the inner surface of the viscosity sensor case, and the inside electrode is vertically separated at a position corresponding to a fixing position where the outside electrode is fixed to the viscosity sensor case.

A viscosity sensor according to another exemplary embodiment of the present invention includes a viscosity sensor case including a vibration tube extended downward, a ring-shaped piezoelectric element disposed inside of the viscosity sensor case, rings disposed to contact an upper surface and an lower surface of the piezoelectric element, and a vibration shaft where a flywheel is mounted to a middle part thereof and a probe is mounted to a lower part thereof. The flywheel is fixed on the ring disposed on piezoelectric element, the probe is mounted to the vibration tube, the probe and the vibration tube exposed in the engine oil are vibrated due to the vibration of the piezoelectric element, and the control portion calculates a viscosity of engine oil on the basis of the damping force of the engine oil generated by the vibration of the probe and the vibration tube.

A plurality of piezoelectric elements may be stacked, and a plurality of the rings are interposed between the piezoelectric elements.

The piezoelectric element of the oil oxidation degree sensor may have a self-cleaning function by vibrating engine oil when the electric current is applied.

A complex sensor according to an exemplary embodiment of the present invention includes a case; the oil level sensor, the oil oxidation degree sensor, the oil viscosity sensor, and the oil temperature sensor installed in the case; and a control portion for calculating measured values according to physical and/or chemical properties inputted from the oil property measuring part. The oil level sensor includes an input electrode having a shape of a pipe and which is installed in the case and is formed such that an electric current is applied thereto, and an oil level electrode disposed apart from the inner surface of the input electrode and which is formed to receive an electric current output from the input electrode. The oil oxidation degree sensor includes the input electrode, and an oil oxidation degree electrode having a shape of pipe and which is disposed at a lower portion of the oil level electrode and formed to receive electric current applied from the input electrode. The oil viscosity sensor includes a viscosity sensor case, a pipe-shaped piezoelectric element, an inside electrode mounted to the inner surface of the piezoelectric element and vertically separated therefrom, an outside electrode mounted to the exterior surface of the piezoelectric element, and a plurality of electric wires for supplying electric power to an inside electrode. One part of the piezoelectric element with the outside electrode is exposed to the engine oil and the other part of the piezoelectric element with the outside electrode is exposed to air, and when electric current is applied thereto the two parts of the piezoelectric element are torsionally vibrated in opposite directions to each other.

The control portion may calculate a capacitance and a dielectric constant of engine oil between the input electrode and the oil level electrode on the basis of the input current of the input electrode and the output current of the oil level electrode, and it calculates an oil level on the basis of the calculated capacitance and dielectric constant of engine oil.

The input electrode may have a shape of a pipe, and the oil level electrode has a shape of a pipe having a smaller diameter than the input electrode.

The oil level electrode is divided into a plurality of parts, and the control portion calculates a plurality of oil levels at the respective divided parts of the oil level electrode on the basis of signals of the output electric current of the oil level electrodes and the input electric current of the input electrode.

The complex sensor may further include a supporting part for mounting the oil level electrode, wherein the supporting part has a shape of a pipe and is made with a material that can be insulated, and the oil level electrode is mounted to the exterior surface of the supporting part.

Four vertical protruded parts may be formed along a longitudinal direction on outer surface of the supporting part, and the vertical protruded parts are disposed between two adjacent divided parts of the oil level electrode so as to insulate respective divided parts of the divided oil level electrode.

A horizontal protruded part may be protruded at the outer surface of the supporting part and at the lower part of the vertical protruded part, and the horizontal protruded part is insulated between the oil level electrode and the oil oxidation degree electrode.

An insert groove may be formed on the horizontal protruded part, and the oil level electrode is fixedly inserted in the insert groove.

The control portion may calculate a relative viscosity of engine oil on the basis of a measured damping force of air and a measured damping force of engine oil.

An inner surface of the viscosity sensor case is projected inward, a longitudinal center of the outside electrode is fixedly mounted to the projected part of the inner surface of the viscosity sensor case, and the inside electrode is vertically separated at a position corresponding to a fixing position where the outside electrode is fixed to the viscosity sensor case.

A complex sensor according to another exemplary embodiment of the present invention include a case; the oil level sensor, the oil oxidation degree sensor, the oil viscosity sensor, and the oil temperature sensor installed in the case; and a control portion for calculating measured values according to physical and/or chemical properties inputted from the oil property measuring part. The oil level sensor includes an input electrode having a shape of pipe installed in the case and formed to be charged with an electric current, and an oil level electrode disposed apart from the inner surface of the input electrode and formed to receive an electric current from the input electrode. The oil oxidation degree sensor includes the input electrode, and an oil oxidation degree electrode having a shape of pipe and which is disposed at a lower portion of the oil level electrode and formed to receive an electric current applied from the input electrode. The oil viscosity sensor includes a viscosity sensor case including a vibration tube extended downward, a ring-shaped piezoelectric element disposed inside of the viscosity sensor case, rings disposed to contact an upper surface and an lower surface of the piezoelectric element, a vibration shaft where a flywheel is mounted to a middle part thereof and a probe is mounted to a lower part thereof, and a control portion that calculates a viscosity of engine oil on the basis of the damping force of the engine oil generated by the vibration of the probe and the vibration tube. The flywheel is fixed on the ring disposed on the piezoelectric element, the probe is mounted to the vibration tube, and the probe and the vibration tube exposed in the engine oil are vibrated due to the vibration of the piezoelectric element.

A plurality of piezoelectric elements may be stacked, and a plurality of the rings may be interposed between the piezoelectric elements.

The case may be formed to have a shape of an inverted "L" ⌐, and may be mounted to a side wall of an engine.

DESCRIPTION OF THE EMBODIMENTS

Figure 1:
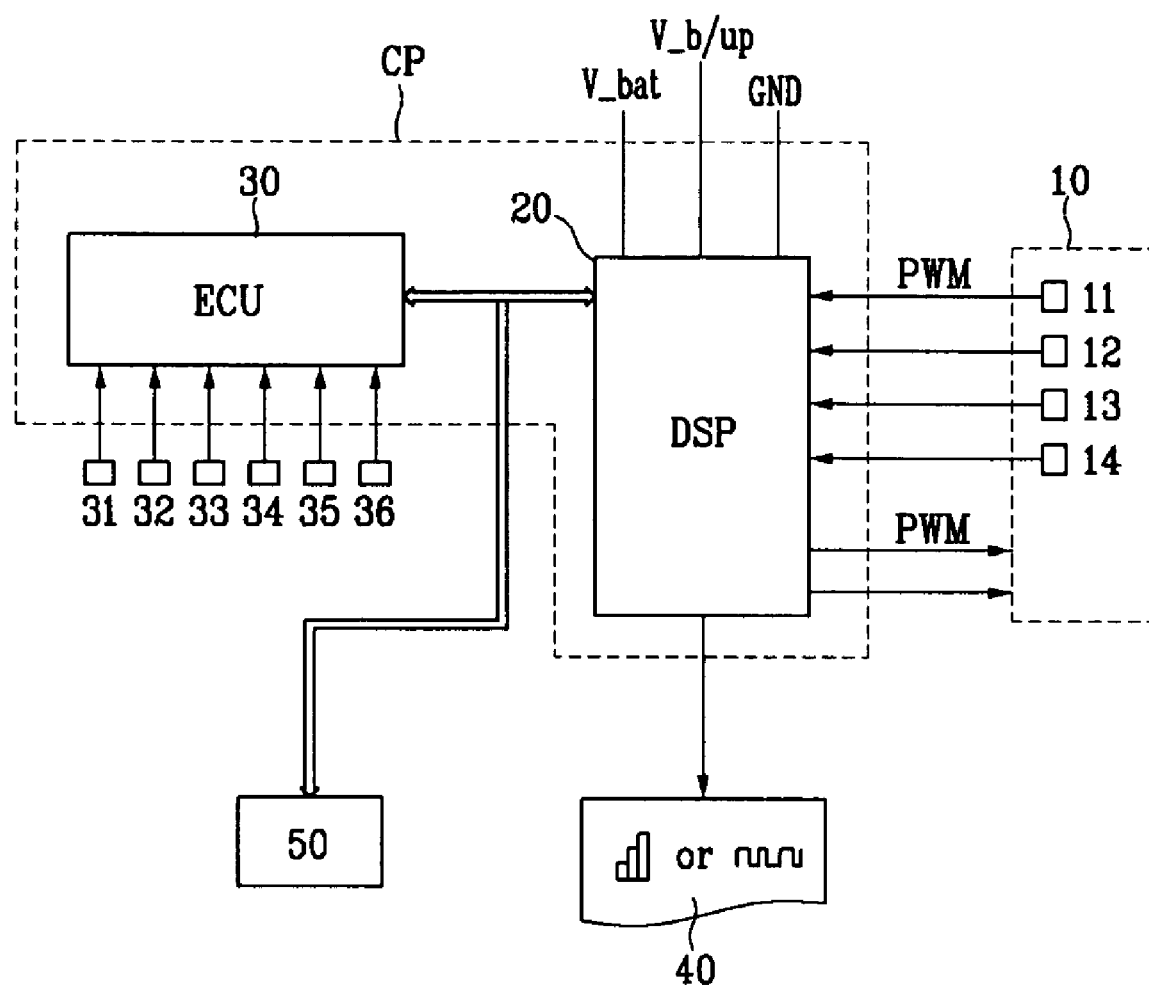
FIG. 1 is a block diagram of an apparatus for scanning engine oil according to an exemplary embodiment of the present invention.

Hereinafter, exemplary embodiments of the present invention will be described in detail with reference to the accompanying drawings.

Referring first to FIGS. 1-6 an exemplary system according to the present invention is described. Reference numeral 20 in the accompanying drawings indicates a DSP (Digital Signal Processor) which is a kind of electronic apparatus. The DSP processes digital signals with input values achieved by measuring changes of physical properties and chemical properties of engine oil with an oil property measuring part. The oil property measuring part may be respective sensors 11 to 14 or a complex sensor 10 in which the sensors 11 to 14 are combined. The DSP stores the history of engine conditions, and properties of engine oil including a degree of oxidation, exchange timing, change history, and level of engine oil. The DSP outputs stored information to an instrument panel 40, a system scanner 50, or an ECU 30, and it calculates information.

In addition, the ECU 30 is an electronic control apparatus having a program for controlling an engine. The ECU 30 is generally the same as an ECU used in a conventional vehicle except as described herein and may include a processor, memory and hardware, software or firmware as may be selected and programmed by a person of ordinary skill in the art based on the teachings of the present invention. The ECU 30 is connected to the DSP 20 through a communication port (which is internationally used) in order to communicate signals with the DSP 20.

The control portion CP, generally includes the ECU 30 and the DSP 20, and is a representative name of an apparatus for storing and calculating data hereinafter.

The ECU 30 is connected with respective driving condition sensors 31 to 36 for receiving various information on driving conditions, like the conventional ECU. A driving condition measuring part includes a vehicle speed sensor 31 for measuring driving speed of the vehicle, an air flow sensor 32 for measuring a quantity of intake air flowing into the engine, a crank angle sensor 33 for measuring engine rotation speed, a TPS (Throttle Position Sensor) 34 for measuring the operation of throttle valve, an idle switch 35 for determining the idle state of the engine, and a switch 36 for determining whether an ignition key is turned on.

The information measured by the driving condition sensors 31 to 36 is inputted to the ECU 30, and the inputted information is used for controlling fuel injection, ignition timing, and accessories (for example alternator, power steering, air conditioner, etc.). Such information is delivered to the DSP 20 from the ECU 20 when required by the DSP 20.

Figure 2:
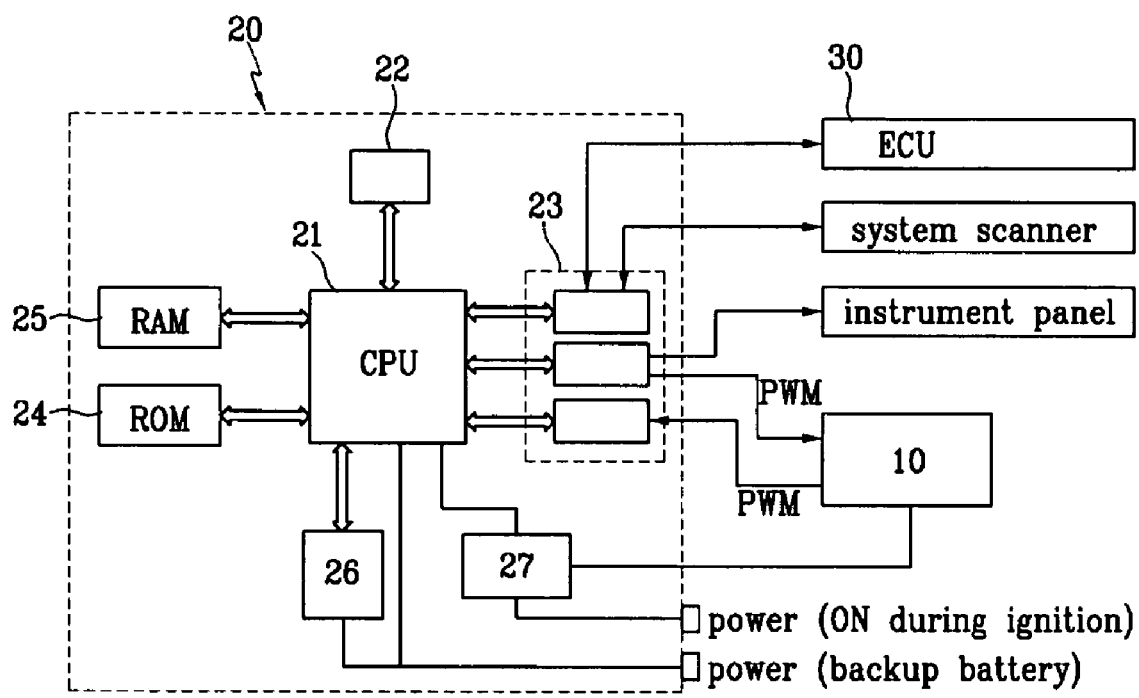
FIG. 2 is a schematic diagram of the DSP (Digital Signal Processor) in the apparatus for scanning engine oil according to an exemplary embodiment of the present invention.

As shown in FIG. 2, the DSP 20 includes a CPU 21, a flash memory 22, input/output port 23, a ROM 24, a RAM 25, a timer 26, and a constant voltage power circuit 27. The CPU 21 compares the measured value of the physical and chemical properties of engine oil which is inputted from the sensors 11 to 14 of the oil property measuring part with a predetermined set of values mapped with adequate properties according to the driving condition of the engine, for determining various things. The flash memory 22 stores measured values delivered from the respective sensors 11 to 14 of the oil property measuring part, and the input/output port 23 delivers a digital signal of the physical and chemical properties measured by the respective sensors 11 to 14 of the oil property measuring part to the CPU 21. The ROM 24 has a program for performing calculation at the CPU 21 therein, the RAM 25 temporarily stores parameters generated in the calculating process of the CPU 21, and the timer 26 provides the time information to the CPU 21. The constant voltage power circuit provides the constant voltage.

The respective sensors 11 to 14 of the oil property measuring part may be integrated into a complex sensor 10 so as to have one body, for the purpose of more efficiently scanning of the engine oil. A signal for control is delivered by PWM (pulse width modulation) between the complex sensor 10 and the DSP 20.

Hereinafter, a complex sensor according to an exemplary embodiment of the present invention will be described, with reference to FIG. 3 to FIG. 5.

The complex sensor 10 according to the present exemplary embodiment of the present invention includes an oil viscosity sensor for measuring physical properties of the engine oil, an oil level sensor, an oil temperature sensor, and an oil oxidation degree sensor for measuring chemical proprieties of the engine oil, so as to measure the amount of change of properties of the engine oil, which are inputted to the DSP 20. That is, the oil viscosity sensor, the oil level sensor, the oil temperature sensor, and the oil oxidation degree sensor are provided to the case 15 having a shape like a pipe.

Firstly, an input electrode 16 formed to have a shape of a pipe is disposed in the case 15. An oil level electrode 12 formed to have a shape of a pipe and having a diameter smaller than that of the input electrode 16 is disposed inside of the input electrode 16, apart from the inner surface of the input electrode 16. Therefore, the oil level sensor according to the present exemplary embodiment of the present invention includes the oil level electrode 12 and the input electrode 16.

An oil oxidation degree electrode 14 is disposed under the oil level electrode 12, and an insulation pipe 17 is disposed between the oil level electrode 12 and the oil oxidation degree electrode 14. The oil oxidation degree electrode 14 has a pipe shape having a smaller diameter than the diameter of the input electrode 16, and it is disposed apart from the inner surface of the input electrode 16. Therefore, the oil oxidation degree sensor according to the present exemplary embodiment of the present invention includes the oil oxidation degree electrode 14 and the input electrode 16.

An oil viscosity sensor 11 for measuring viscosity of the engine oil is disposed inside the oil oxidation degree electrode 14, and an oil temperature sensor 13 is provided outside of the case 15.

At the side wall of the case 15 and the input electrode 16, a plurality of oil holes 15a and 16a are formed, such that engine oil at the outside of the case 15 flows into the inside of the case 15 through the holes.

The input electrode 16 is provided such that current from the battery flows into the input electrode 16, and then the electric current is induced from the input electrode 16 to the oil level electrode 12 and oil oxidation degree electrode 14. The electric current induced from the input electrode 16 to the oil level electrode 12 and oil oxidation degree electrode 14 is applied to a substrate 18 through an electric wire.

The oil viscosity sensor 11 is provided such that an electric current from the battery is applied to the viscosity sensor 11, and the electric current flows to the substrate 18 through a piezoelectric element 11a. The oil viscosity sensor 11 is supported at the inside of the oil oxidation degree sensor 14 by an O-ring 19 formed of rubber.

The oil viscosity sensor 11 for measuring a change of the oil viscosity uses a characteristic of a vibration of the piezoelectric element 11a so as to measure viscosity of the engine oil. That is, the piezoelectric element 11a is vibrated due to its characteristics, when a voltage is applied thereto. The piezoelectric element may be formed with PbO, ZrO2, TiO2, PbTiO3, or PbNb2O6, etc. The piezoelectric element is installed such that one aspect of the piezoelectric element is in contact with engine oil and the other aspect is in contact with air. The aspect of the piezoelectric element 11a contacting with the engine oil may have a metal membrane 11b provided to cover the exterior surface of the piezoelectric element so as to protect the piezoelectric element 11a.

Hereinafter, a principal of measuring viscosity of engine oil using the piezoelectric element will be described. Firstly, a voltage is applied to the electrode of the piezoelectric element so as to vibrate the piezoelectric element, in order to measure a shear force of a fluid. Here, a damping force varies according to the viscosity of the contacting fluid. Therefore, the viscosity of the fluid can be determined by using this property. A circuit of a sensor terminal may be equivalent to a series circuit of reactance and impedance. That is, the viscosity of engine oil is measured by calculating and measuring a change of the reactance and impedance.

The oil viscosity sensor 11 additionally has a self-cleaning function as well as the function of measuring viscosity of engine oil. Generally, inside of a complex sensor 10, as time passes, the sensor becomes contaminated by various deposits. Since the oil viscosity sensor 11 is disposed inside of the pipe-shaped case 15, the vibration of the piezoelectric element 11a can perform a self-cleaning function. That is, the vibration generated by the piezoelectric element 11a when as electric current periodically flows therethrough causes a fluctuation of the engine oil and detaches foreign particles from the surface of the sensor.

An additional function of the piezoelectric element 11a is a function of increasing accuracy of measuring the engine oil level. That is, the oil level is calculated by measuring return time of a supersonic wave which is periodically emitted. Therefore, the oil level is revised and the accuracy is improved by comparing the oil level measured in such a method with the oil level measured with the oil level sensor.

Figure 6:
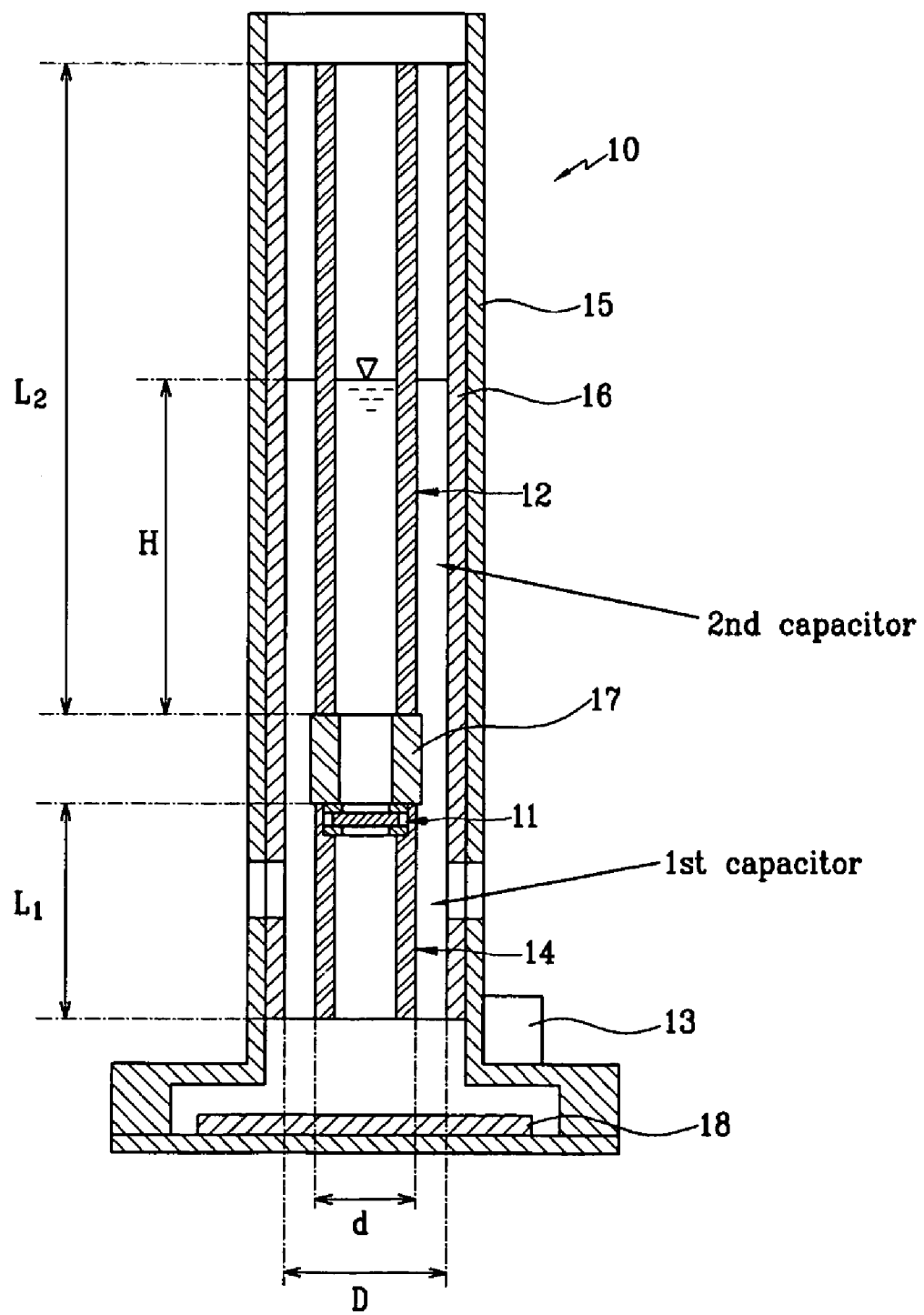
FIG. 6 is a cross-sectional view of a sensor illustrating a method for calculating a digital value of an oil level and a degree of oxidation of engine oil according to an exemplary embodiment of the present invention.

Hereinafter, referring to FIG. 6, principals of measuring the degree of oxidation and the oil level using the complex sensor will be described in detail.

A degree of oxidation is measured by the oil oxidation degree sensor on the basis of the dielectric constant which is calculated based on the capacitance between the two pipe-shaped electrodes (indicated as reference numerals 14 and 16 in the drawing). In addition, other chemical properties, for example acid level, alkali level, TBN, etc., can also be measured by the oxidation sensor on the basis of the dielectric constant. The two pipe-shaped electrodes are formed of metal, and have smooth surfaces. According to such an oil oxidation degree sensor, deterioration of the sensor due to a secular change doesn't occur compared with a conventional oil oxidation degree sensor. The conventional oil oxidation degree sensor uses a method of merely measuring capacity of the oil, and the surface of the pipes are periodically cleaned due to the vibration of the piezoelectric element. The main principals for measuring properties of engine oil are as follows.

1) A Capacitance Between Two Pipes

A capacitance of a capacitor formed with two pipes (the diameter of the larger one is D, the diameter of the smaller one is d, and the length is L) and filled with a material having a certain dielectric constant is determined according to the following Equation 1.

$$C = 2\pi\varepsilon \frac{L}{\ln(D/d)} \propto \varepsilon \cdot L \qquad \text{Equation 1}$$

That is, the capacitance is in proportion to the dielectric constant and the length of the pipe.

When a dielectric constant of a vacuum state is 1, dielectric constants of respective dielectric materials are shown in the table below.

| Material | Dielectric constant($\in$) | Material | Dielectric constant($\in$) |
|---|---|---|---|
| air (1 atm) | 1.00054 | Water (20° C.) | 80.4 |
| engine oil | 2-6 | Water (25° C.) | 78.5 |

The dielectric constant of engine oil varies according to the viscosity and proportion of other additives, but is always less than that of water and more than that of air. Generally, as antioxidants decrease, the dielectric constant gradually increases. In addition, when coolant flows into the engine oil, the dielectric constant rapidly increases. On the basis of such phenomenon, properties of engine oil are measured as follows.

Figure 5:
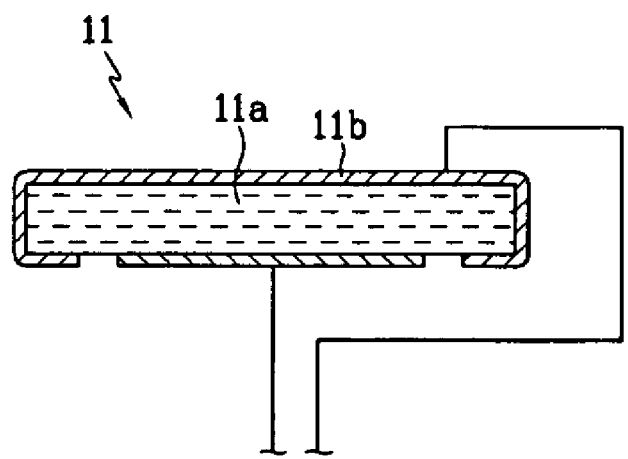
FIG. 5 is a schematic cross-sectional view of the oil viscosity sensor of FIG. 4.

As shown in FIG. 5, the oil oxidation degree electrodes 14 is submerged in the engine oil. The capacitance of new engine oil (having a dielectric constant $\in$NEW) at a first capacitor is given by the following Equation 2:

$$C_{1,NEW} = 2\pi\varepsilon_{NEW} \frac{L_1}{\ln(D/d)} = \alpha \cdot \varepsilon_{NEW} \qquad \text{Equation 2}$$

where α is a constant.

The capacitance of used engine oil (having a dielectric constant ∈USED) at the first capacitor is given by the following Equation 3.

$$C_{1,USED} = 2\pi\varepsilon_{USED}\frac{L_1}{\ln(D/d)} = \alpha \cdot \varepsilon_{USED} \quad \text{Equation 3}$$

The change of capacitance is given by the following Equation 4.

$$\Delta C = C_{1,USED} - C_{1,NEW} = \alpha \cdot (\varepsilon_{USED} - \varepsilon_{NEW}) \quad \text{Equation 4}$$

Engine oil is determined to be new oil when the electrode 12 of the oil level sensor is exposed to air, and it is determined as a time to exchange engine oil when the capacitance is rapidly changed during driving. A principal for measuring oil level is as follows.

The oil level sensor has the electrode 12 which is partially submerged in the engine oil. Therefore, the oil level sensor can be considered as two kinds of capacitor installed in parallel, because the capacitor has two kinds of dielectric materials (air, oil).

Capacitance of the second capacitor is given by the following Equation 5.

$$C_2 = C_{2,air} + C_{2,oil} = 2\pi\varepsilon_{oil}\frac{L_2 - h}{\ln(D/d)} + 2\pi\varepsilon_{oil}\frac{h}{\ln(D/d)} \quad \text{Equation 5}$$

Here, the dielectric constant of air is 1, and the dielectric constant of oil is determined by the first capacitor.

$$C_1 = 2\pi\varepsilon_{oil}\frac{L_1}{\ln(D/d)} \quad \text{Equation 6}$$

Oil level h is calculated as follows.

$$h = \frac{C_2/L_2 - 2\pi/\ln(D/d)}{C_1/L_1 - 2\pi/\ln(D/d)} L_2 \quad \text{Equation 7}$$

In addition, an oil temperature sensor 13 may be a resistance thermometer (for example, PT1000, NTC, etc.). The temperature is measured by measuring a change of resistance according to temperature, and by transforming the measured change of resistance to electrical signals through a bridge circuit.

Amounts of change of physical and chemical properties of engine oil detected by such a complex sensor 10 are converted to digital signals, and are stored in the flash memory 22 installed in the DSP 20. The amount of change of the physical and chemical properties is calculated with information of engine operation inputted from the ECU 30 through an input/output port.

In the DSP 20, a predetermined value is set to suggest an optimum state of the engine oil on the basis of information of engine operation inputted from the ECU 30. Such a set predetermined value is experimentally determined using a dynamometer with an engine, and by analysis of various engine oils and various engine conditions.

Hereinafter, a complex sensor according to another exemplary embodiment will be described with reference to FIG. 8 to FIG. 12.

Figure 8:
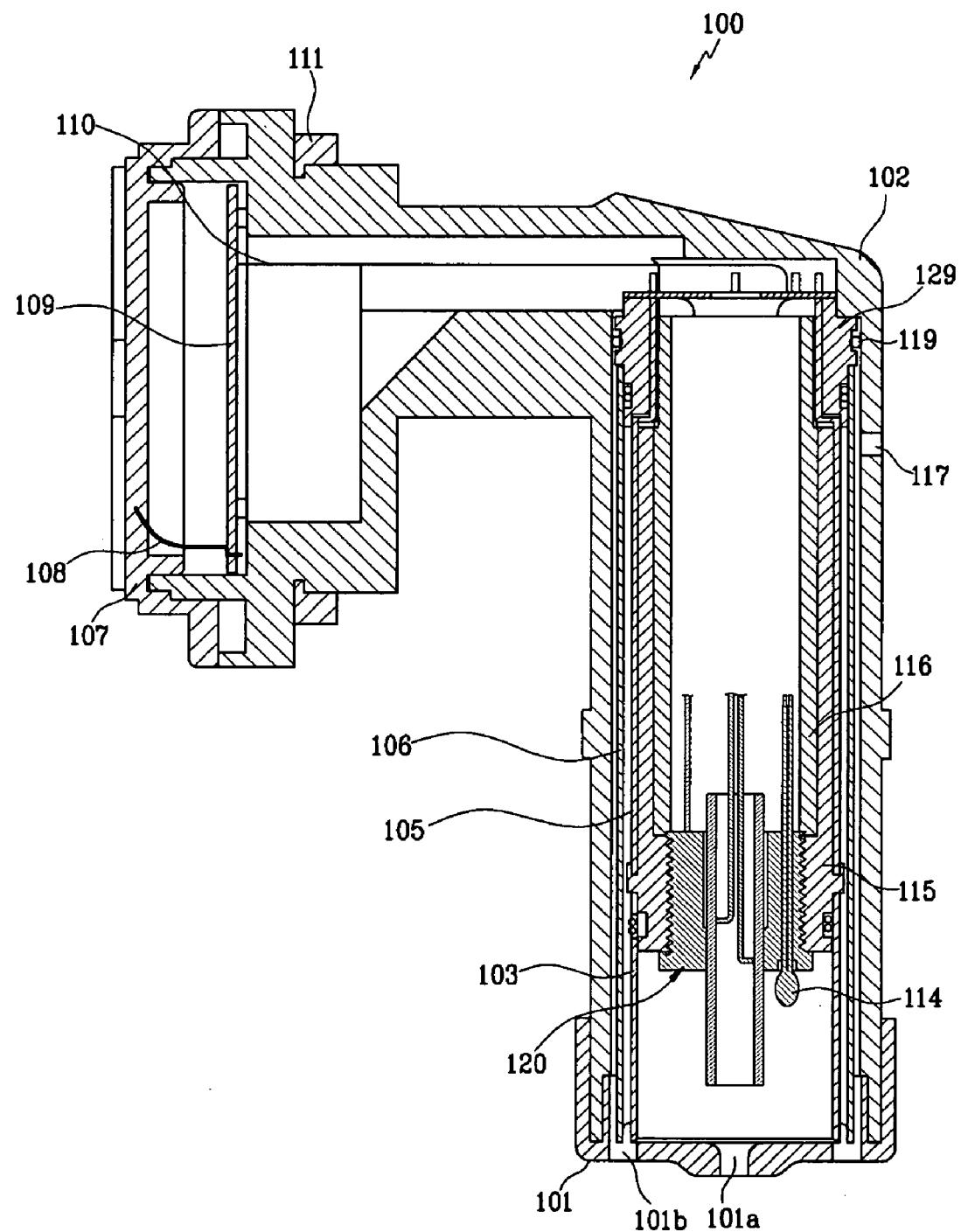
FIG. 8 is a cross-sectional view of a complex sensor according to an exemplary embodiment of the present invention.
Figure 9:
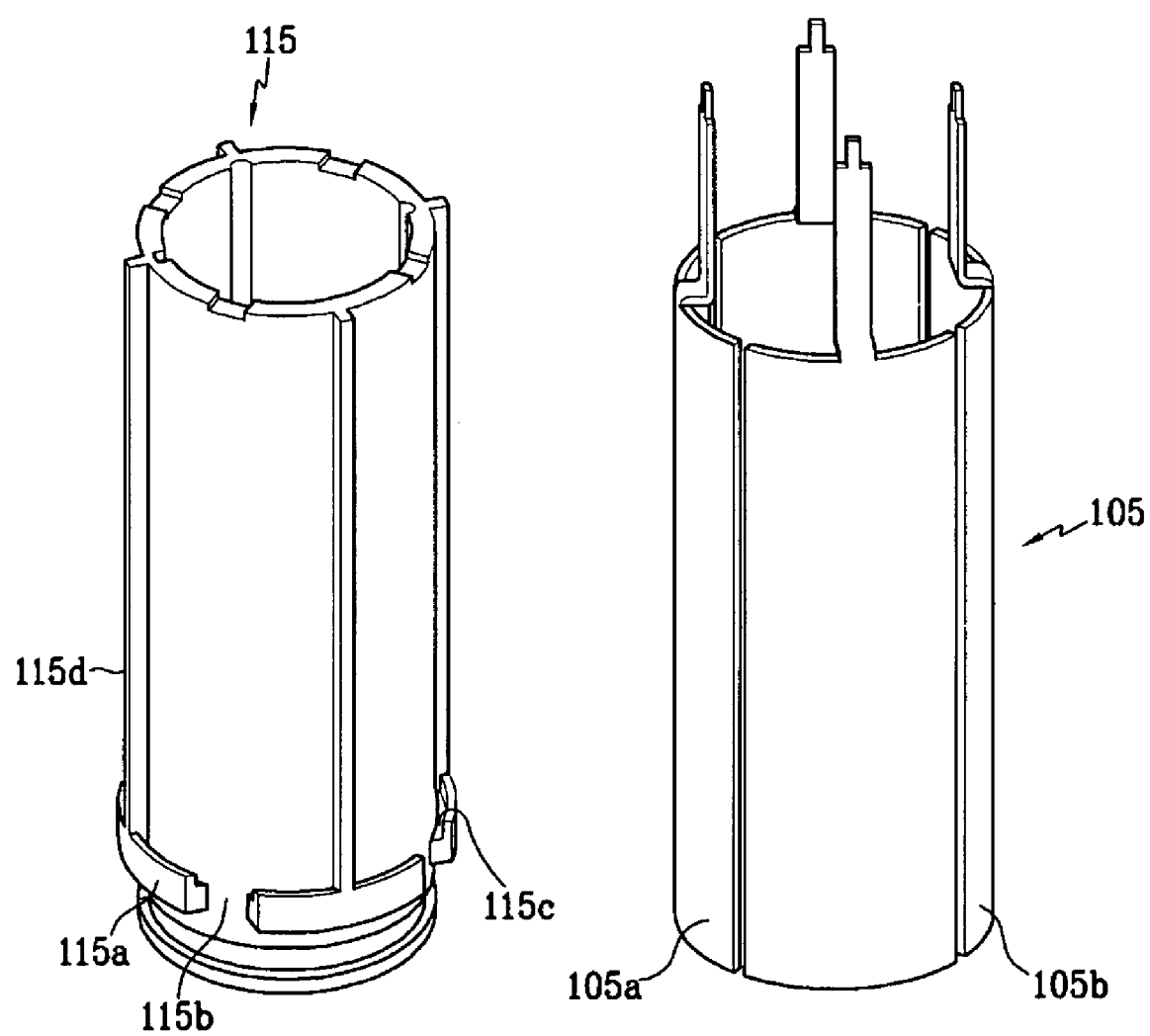
FIG. 9 is a perspective view of a supporting part and a level electrode according to an exemplary embodiment of the present invention.
Figure 10:
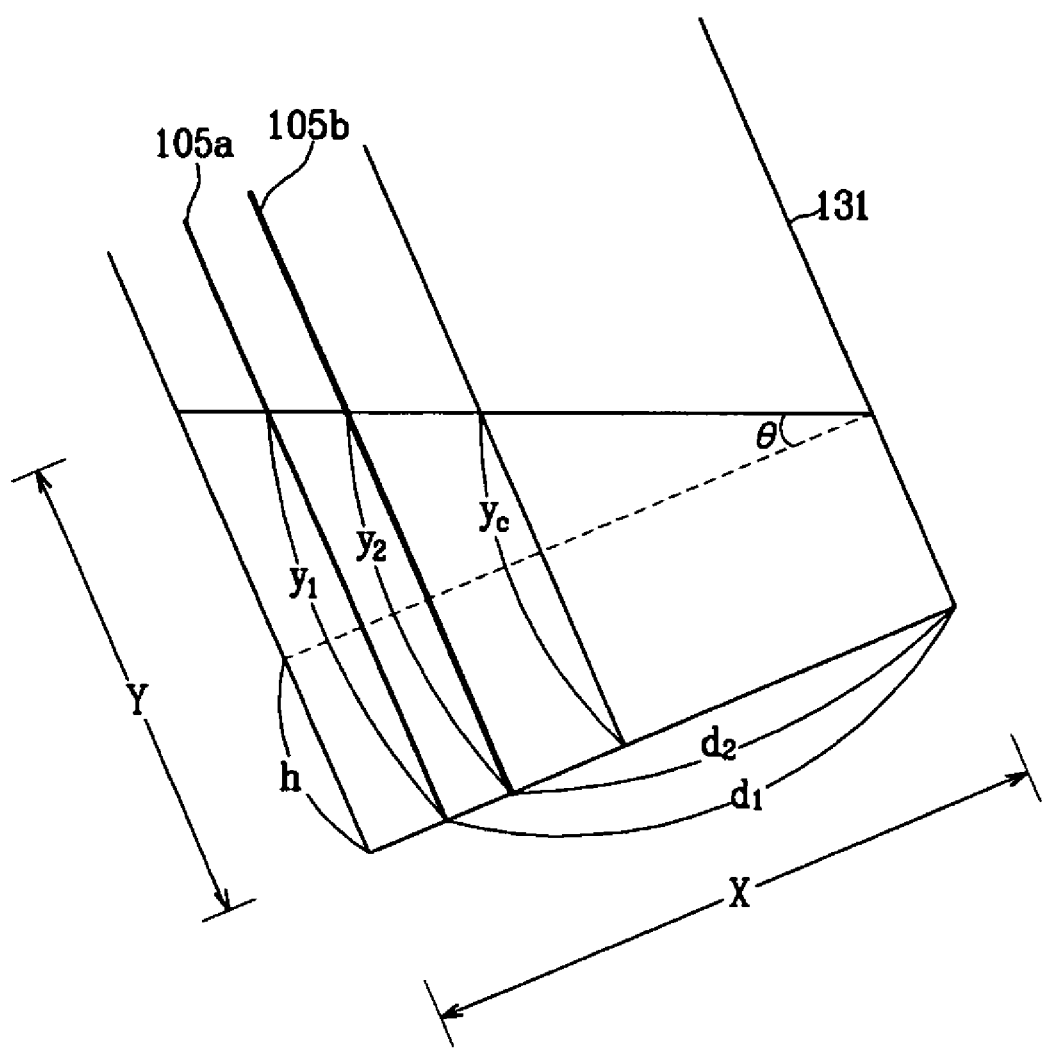
FIG. 10 is a schematic diagram of an oil level sensor according to an exemplary embodiment of the present invention.
Figure 11:
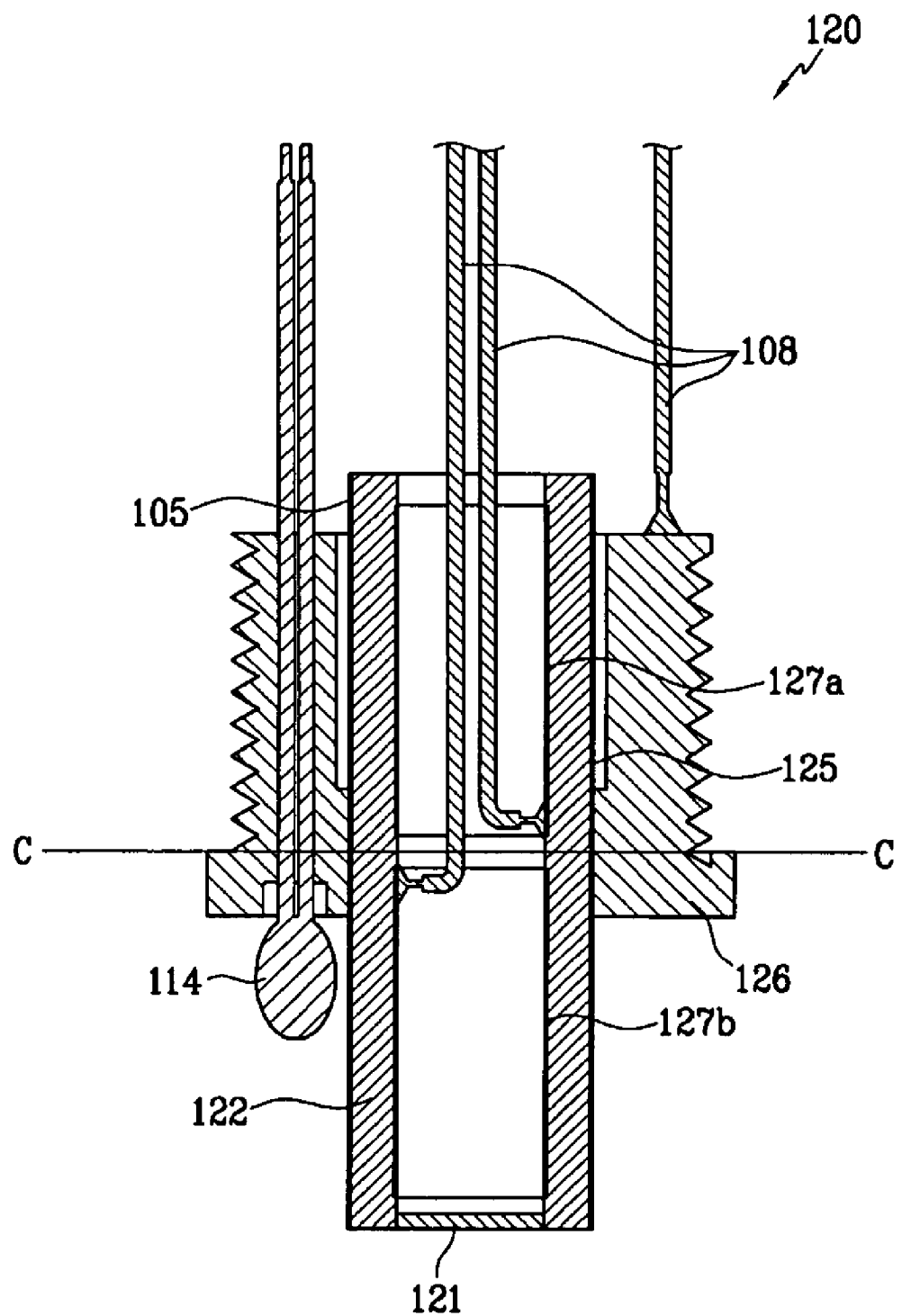
FIG. 11 is an enlarged cross-sectional view of a viscosity sensor shown in FIG. 9.
Figure 12:
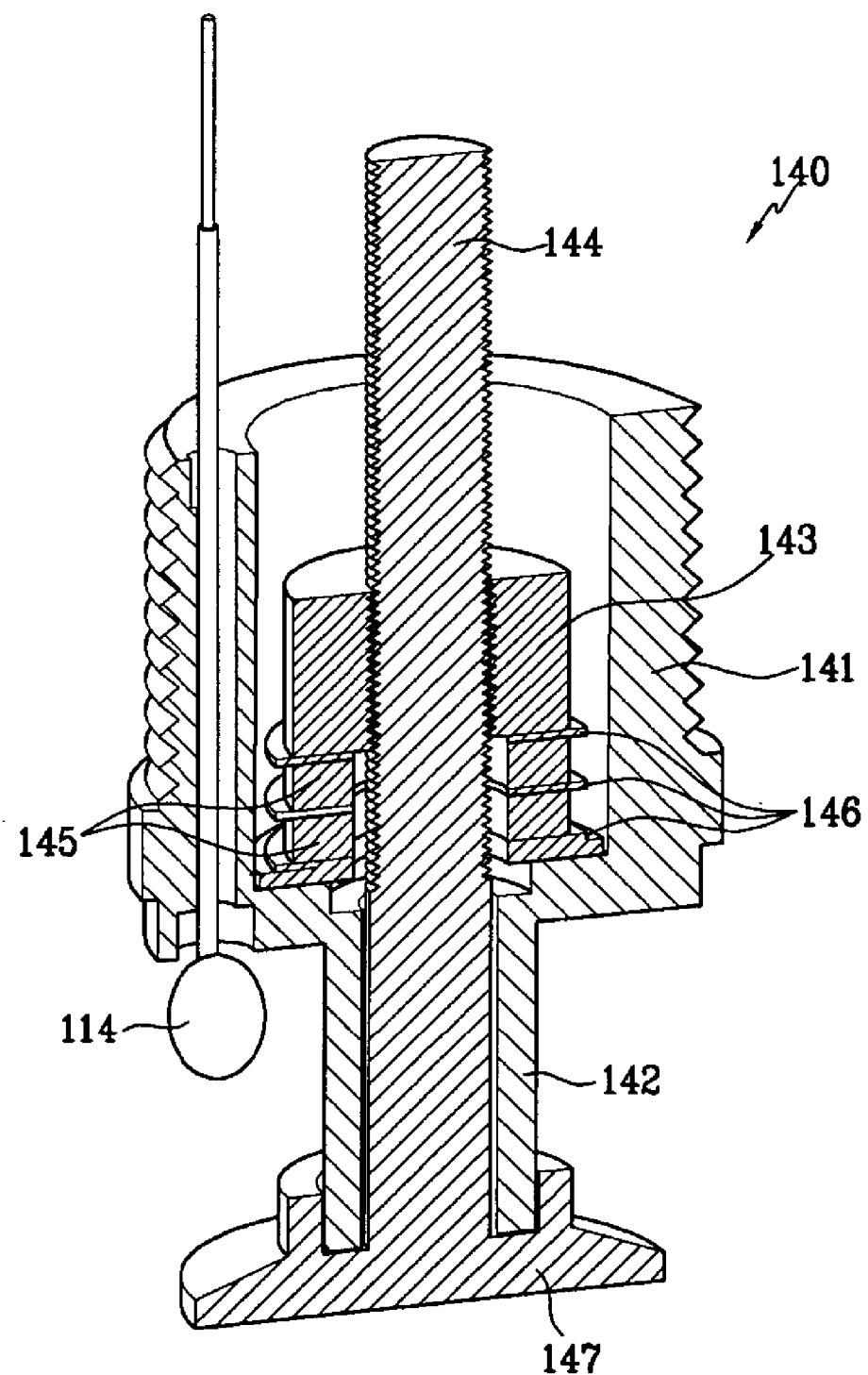
FIG. 12 is a cross-sectional view of a viscosity sensor according to an exemplary embodiment of the present invention.

FIG. 8 is a cross-sectional view of a complex sensor 100 according to another exemplary embodiment of the present invention, FIG. 9 is a perspective view of a supporting part and a level electrode according to an exemplary embodiment of the present invention, FIG. 10 is a schematic diagram of an oil level sensor according to an exemplary embodiment of the present invention, FIG. 11 is an enlarged cross-sectional view of a viscosity sensor shown in FIG. 9, and FIG. 12 is a cross-sectional view of a viscosity sensor according to an exemplary embodiment of the present invention.

A complex sensor 100 according to this embodiment of the present invention includes a case 102 having a shape of an inverted "L" (⌐), and a cap 101 combined with the lower part of the case 102, as shown in FIG. 8. Inside of the case 102, an input electrode 106 having a shape of a pipe is provided. The input electrode 106 is mounted on the cap 101. Inside of the input electrode 106, an oil oxidation degree electrode 103 having a smaller diameter than a diameter of the input electrode 106 is disposed. The oil oxidation degree electrode 103 is also mounted on the cap 101.

The oil oxidation degree sensor according to the present exemplary embodiment of the present invention includes the oil oxidation degree sensor 103 and the input electrode 106.

At the upper part of the oil oxidation degree electrode 103, an oil level electrode 105 is disposed.

The oil level electrode 105 has a smaller diameter than the input electrode 106, like the oil oxidation degree electrode 103. The oil level electrode 105 has a shape of a divided pipe which will be described later.

Inside of the oil level electrode 105 and the oil oxidation degree electrode 103, a supporting part 115 having a shape of a pipe is disposed, and the oil viscosity sensor 120 and the temperature sensor 114 are disposed inside of the supporting part 115.

Hereinafter, a structure of the complex sensor will be described in more detail.

Firstly, a structure of the oil level sensor will be described.

The oil level sensor is disposed in the case 102. The oil level sensor has an input electrode 106 having a shape of a pipe and is installed to have an electric current applied thereto, and an oil level electrode 105 having a shape of a pipe installed apart from the inner surface of the input electrode 106 so as to receive the electric current from the input electrode 106.

The oil level electrode 105 is mounted to the exterior circumference of the supporting part 115, and may be formed to have a shape of a divided metal pipe with respect to the cross-sectional view, as shown in FIG. 9.

FIG. 9 is a perspective view of the supporting part 115 and the oil level electrode 105 separated from the complex sensor.

Here, the supporting part 115 is a pipe for supporting the oil level electrode 105, and the oil level electrode 105 has a shape of a pipe divided into four parts.

On the exterior circumference of the supporting part 115, four vertical protruded parts 115d are formed to be vertically protruded, and four horizontal protruded parts 115a are formed to be vertically protruded at the lower part of the vertical protruded parts.

Between the horizontal protruded part 115a and the exterior circumference of the supporting part 115, an insert groove 115c is formed. The pipe-shaped oil level electrode 105 is fixedly inserted into the insert groove 115c.

The vertical protruded parts 115d insulate the respective adjacent divided parts of the oil level electrode 105.

The four horizontal protruded parts 115a are disposed apart from each other, and oil pathways are formed between adjacent protruded parts 115b.

The oil level sensor having such a structure additionally includes a control portion, and oil level is determined with respect to the control portion.

The oil level is calculated on the basis of the capacitance and dielectric constant measured between the oil level electrode 105 and the input electrode 106.

In this embodiment, a method for calculating oil level is the same as in the above-described exemplary embodiment of the present invention.

However, according to the oil level sensor of this exemplary embodiment of the present invention, oil level is measured at four positions. Therefore, by using four oil levels at four positions, a gradient of the vehicle can be determined. In addition, using such an oil level sensor, rolling angle of the vehicle, pitching angle of the vehicle, etc., can be measured, and the measurement can be used for controlling stability of the vehicle. In addition, on the basis of the four oil levels, the amount of engine oil can be determined.

FIG. 10 shows a schematic cross-sectional view of the engine and the oil level sensor according to this embodiment of the present invention. Reference numeral 131 indicates an engine. Reference numerals 105a and 105b indicate two oil level electrodes facing each other.

y1 is an oil level measured at the first oil level electrode 105a, y2 is an oil level measured at the second level electrode 105b, yc is an oil level measured at the central part of the engine, X is a length of an arbitrary horizontal line from one end to the other end of the lower surface of the engine, d1 is a distance from one end of the engine to the second level electrode, d1 is a distance from one end of the engine to the first level electrode, θ is a gradient of the engine, Y is the highest height from the bottom surface of the engine, and h is the lowest height from the bottom surface of the engine.

$$y1-h:d1=y2-h:d2 \qquad \text{Equation 8}$$

Here, y1 and y2 are measure values of the oil level. Values d1 and d2 are predetermined when the engine is designed. Therefore, a value h can be calculated easily.

In addition, $$y2-h:d2=yc-h:1/2*X \qquad \text{Equation 9}$$

Here, since y2 is a measured value, h is a value calculated by Equation 8, and X is a predetermined value when an engine is designed, yc can be determined. Since yc is a value of height at the central part of the engine, when a vehicle is tilted, the oil level at the center part of the engine can be determined.

$$\tan \theta=(Y-h)/X \qquad \text{Equation 10}$$

In addition, a gradient of the vehicle θ can be easily determined using Equation 10. When the gradient of the vehicle θ is known, rolling angle and pitching angle can be determined. Therefore, the gradient of the vehicle θ can be used for controlling stability of the vehicle. In addition, the amount of engine oil can be calculated by multiplying yc with an area of the bottom surface of the engine.

The above-mentioned Equations 8 to 10 are exemplary equations for calculating the engine oil level, the amount of engine oil, and a gradient of the vehicle, and the method is not limited to such exemplary equations.

Hereinafter, the oil oxidation degree sensor will be described.

An oil oxidation degree sensor according to the exemplary embodiment of the present invention includes the input electrode 106, and the oil oxidation degree electrode 103.

That is, the input electrode 106 construct an oil level sensor with the oil level electrode 105, and constructs the oil oxidation degree sensor with the oil oxidation degree electrode 103.

The oil oxidation degree electrode 103 is disposed in the input electrode 106 apart from the inner surface of the input electrode 106. In addition, the oil oxidation degree electrode 103 is mounted to the lower part of the supporting part 115 so as to be disposed at the lower part of the oil level electrode 105. The oil oxidation degree electrode 103 is insulated from the oil level electrode 105 due to the horizontal protruded part 115a disposed therebetween.

The oil oxidation degree electrode 103 has a smaller diameter than the input electrode 106 so as to be disposed apart from the inner surface of the input electrode 106.

Therefore, the oil oxidation degree electrode 103 and the input electrode 106 have a shape of a double pipe, and a space for the engine oil is formed between the two pipe-shaped electrodes. It is preferable that the oil oxidation degree electrode 103 is made with a metal like that of the input electrode 106.

When engine oil is supplied to the engine, the engine oil passes through a second inlet 101b, a space formed between the input electrode 106 and the oil oxidation degree electrode 103, and a space formed between the input electrode 106 and the oil level electrode 105, in order. Air between the input electrode 106 and the oil level electrode 105 goes out of the complex sensor through an air hole 117.

Since the oil oxidation degree sensor has such a structure, a capacitance of the engine oil flowing into the space between the input electrode 106 and the oil oxidation degree electrode 103 through the second inlet 101b can be measured, and chemical properties of the engine oil including the degree of oxidation are measured on the basis of the dielectric constant determined by using the capacitance of the engine oil.

A method for calculating the capacitance and dielectric constant of engine oil and calculating the chemical properties including the degree of oxidation according to this embodiment of the present invention is the same as in the above-mentioned embodiment of the present invention.

Hereinafter, referring to FIGS. 8, 11, and 12, the oil viscosity sensor 120 will be described in more detail.

The oil viscosity sensor 120, as shown is FIG. 11, is installed in the oil oxidation degree electrode 103 and the oil level electrode 105. The oil viscosity sensor 120 is fixed inside of the supporting part 1115 and has a shape of a pipe.

Therefore, the oil level electrode 105 and the oil oxidation degree electrode 103 are mounted to an outer part of the supporting part 115, and a viscosity sensor case 126 is mounted to an inner part of the supporting part 115.

The supporting part 115 is preferably made with a material that can be insulated.

The oil viscosity sensor 120 according to the exemplary embodiment of the present invention includes a piezoelectric element 122 having a shape of a pipe, a first inside electrode 127a and a second inside electrode 127b mounted on the inner surface of the piezoelectric element 122, and an outside electrode 125 mounted on the outer surface of the piezoelectric element 122. The piezoelectric element 122 mounted with the first and second inside electrode 127a and 127b and the outside electrode 125 is installed in a viscosity sensor case 126. The sensor case 126 may be formed with a metal.

A lower part of the viscosity sensor case 126 is protruded to the inside and a longitudinal center of the outside electrode 125 is fixed with the protruded portion of the viscosity sensor case 126. Since the piezoelectric element 122 is torsionally vibrated with respect to its longitudinal center portion, it is preferable that the longitudinal center of the piezoelectric element 122 is fixed.

The inside electrodes 127a and 127b are apart from each other in the longitudinal direction, and each of them is connected to the exterior power supply through an electric wire 108.

A sealing element 121 is mounted to the lower part of the oil viscosity sensor so as to prevent inflow of the engine oil into the sensor.

The lower part of the oil viscosity sensor 120 is submerged in the engine oil that flows into the case 102 through a first inlet hole 101a, as shown in FIG. 8. However, the upper part of the viscosity sensor 120 is exposed to air due to the sealed structure.

Figure 3:
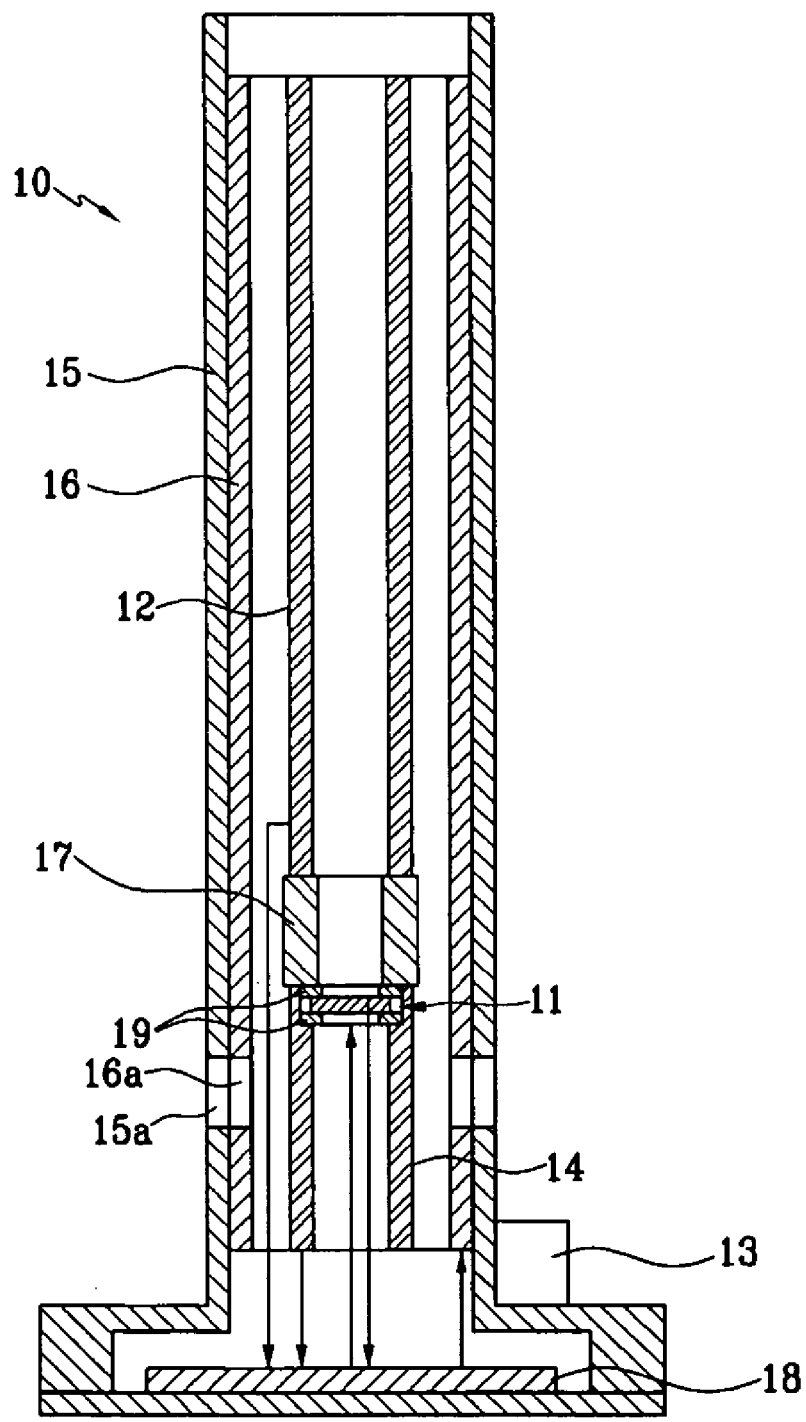
FIG. 3 is a schematic cross-sectional view of a complex sensor according to an exemplary embodiment of the present invention.
Figure 4:
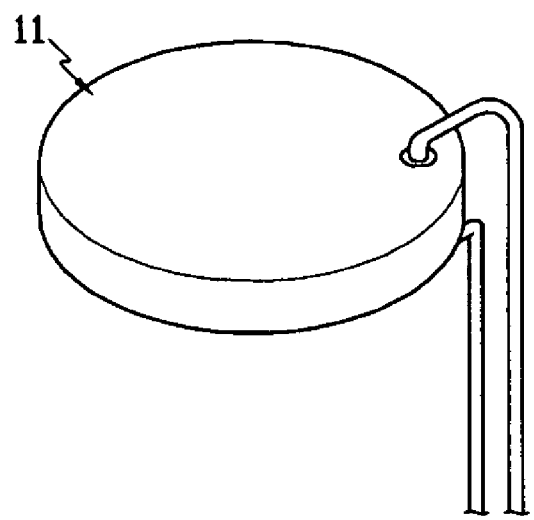
FIG. 4 is a schematic perspective view of the oil viscosity sensor installed in the complex sensor of FIG. 3.

In such a state, when AC voltage is applied to the first and second electrodes 127a and 127b, the upper part of the piezoelectric element 122 above a line C-C in FIG. 11 and the lower part of the piezoelectric element 122 below the line C-C in FIG. 3 are torsionally vibrated in opposite directions to each other. The vibration of the piezoelectric element 122 is reduced by a damping force of the fluid. Since the damping force of the fluid varies according to the viscosity of the fluid, viscosity of the fluid can be determined by using the damping force.

It is preferable to determine a relative viscosity by comparing the damping force of air and the damping force of engine oil, or by comparing the viscosity of air and the viscosity of engine oil. In a case that a secular change occurs in the piezoelectric element 122, if the absolute viscosity of the engine oil is merely measured, reducing errors caused by the secular change is difficult. However, if the relative viscosity of engine oil to air is used for estimating the quality of engine oil, the error caused by the secular change can be reduced.

Actually, since the piezoelectric element 122 vibrates in an elastic range, a secular change of the piezoelectric element seldom occurs. If it does occur, the accuracy can be increased by adapting such a method for measuring relative viscosity of engine oil.

An oil viscosity sensor may be constructed as shown in FIG. 12.

According to an exemplary oil viscosity sensor 140 of the present invention, as shown in FIG. 12, the lower part of the viscosity sensor case 141 is extended downward to form a vibration tube 142 having a shape of a pipe. Inside of the viscosity sensor case 141, a ring-shaped piezoelectric element 145 is disposed.

A plurality of piezoelectric elements 145 can be used for magnifying a vibration angle. At the top and bottom surfaces of the piezoelectric element 145, rings 146 for applying an electric current to the piezoelectric element are disposed. The rings 146 may be formed with copper. The rings 146 deliver an electric current to the piezoelectric element 145, and cause an up-and-down vibration of the piezoelectric element 145.

A flywheel 143 is provided on the piezoelectric element 145 so as to adjust or control the natural frequency. The flywheel 143 is fixedly mounted to an exterior circumference of the vibration shaft 144, and may be integrally formed with the vibration shaft 144.

Natural frequency is a function of a moment of inertia, and the moment of inertia is equal to $\frac{1}{2}*mr^2$ (m: mass of flywheel, r: radius of flywheel). Therefore, according to the mass and size of the flywheel 143, the natural frequency varies.

The vibration shaft 144 is longitudinally disposed at the central part of the viscosity sensor case 141 along a longitudinal direction so as to penetrate the ring-shaped piezoelectric element 145 and the vibration tube 142.

A lower part of the vibration shaft 144 is mounted to a probe 147 at the lower exterior part of the viscosity sensor case 141. The vibration shaft 144 and the probe 147 may be integrally formed.

The probe 147 is fixed with the vibration tube 142, and is exposed to the engine oil at the outside of the viscosity sensor case 141 so as to directly contact the engine oil.

Hereinafter, a principle of an operation of the oil viscosity sensor will be described.

When AC voltage is applied to the piezoelectric element 145 through the ring 146, a vibration of the piezoelectric element 145 is delivered to the vibration shaft 144 through the flywheel 143.

Then, the micro-torsional vibration of the vibration shaft 144 is delivered to the probe 147 and the vibration tube 142. At this time, since the probe 147 and the vibration tube 142 are contacted with engine oil, the vibration can be delivered to the engine oil from the probe 147 and the vibration tube 142. Therefore, by measuring the damping force of the engine oil, viscosity of engine oil can be determined.

Reference numeral 114 in FIG. 8, FIG. 11, and FIG. 12 indicates a temperature sensor. The oil temperature sensor 114 is a resistance thermometer (for example, PT1000, NTC, etc.). A temperature is measured by measuring a change of resistance according to temperature, and by transforming the measured change of resistance to electrical signals through a bridge circuit.

The above-described input electrode, level sensor, oil oxidation degree sensor, oil viscosity sensor, and temperature sensor may be combined in a case 102, as shown in FIG. 8, so as to construct the complex sensor, or may be separately installed so as to construct respective independent sensors.

That is, each of the sensors can be used independently, and can be used as a component of the complex sensor when the sensors are combined. Hereinafter, other components constructing the complex sensor, in addition to the above-mentioned four sensors, will be described.

Firstly, the case 102 is formed to have a shape of and inverted "L" (⌐). Therefore, when the complex sensor is mounted to the side wall of an oil pan, the mounting structure can be more stable against external impact. A cap 101 is mounted to the lower part of the case 102.

The case 102 may be mounted to the oil pan with a body O-ring 111 by a bolt.

A first inlet 101a is formed at the center of the cap 101 such that engine oil flows into the oil viscosity sensor, and a second inlet 101b is formed at the edge portion of the cap 101 such that engine oil flows into the oil oxidation degree sensor (between two electrodes 103 and 106) and oil level sensor (between two electrodes 105 and 106). At the side wall of the case 102, an air hole 117 to let out the air is formed, as shown in FIG. 8.

Therefore, engine oil flowing into the case through the first inlet 101a and the second inlet 101b flows upward through the four oil pathways 115b formed at the supporting part 1115, as shown in FIG. 9.

A circuit 109 is mounted in the case 102.

A cover 107 is mounted to an end of the case 102 so as to protect the circuit 109, and has a radiation pin so as to radiate heat generated at the circuit 109.

A ground spring 108 is connected with the circuit 109 and the cover 107, and acts as a ground for the circuit 109.

A flexible cable 110 is connected to the oil viscosity sensor 120, the temperature sensor 114, the oil oxidation degree sensor, and the oil level sensor, and delivers an electric signal to the circuit 109.

The body O-ring 111 is mounted to the case 102, and prevents leakage of the engine oil between the oil pan 30 and the case 102.

An upper supporting part 129 is mounted to the supporting part 115, and supports the oil level sensor and the flexible cable 110.

A sub O-ring 119 is mounted to the upper supporting part 129, and prevents reverse flow of the engine oil.

Inside of the case 102, the pipe-shaped input electrode 106 is disposed. The input electrode 106 is formed with a conductive material, for example a metal. The input electrode 106 is mounted on the cap 101.

Hereinafter, a method for scanning engine oil using the apparatus for scanning engine oil including the above-mentioned sensors will be described.

Figure 7:
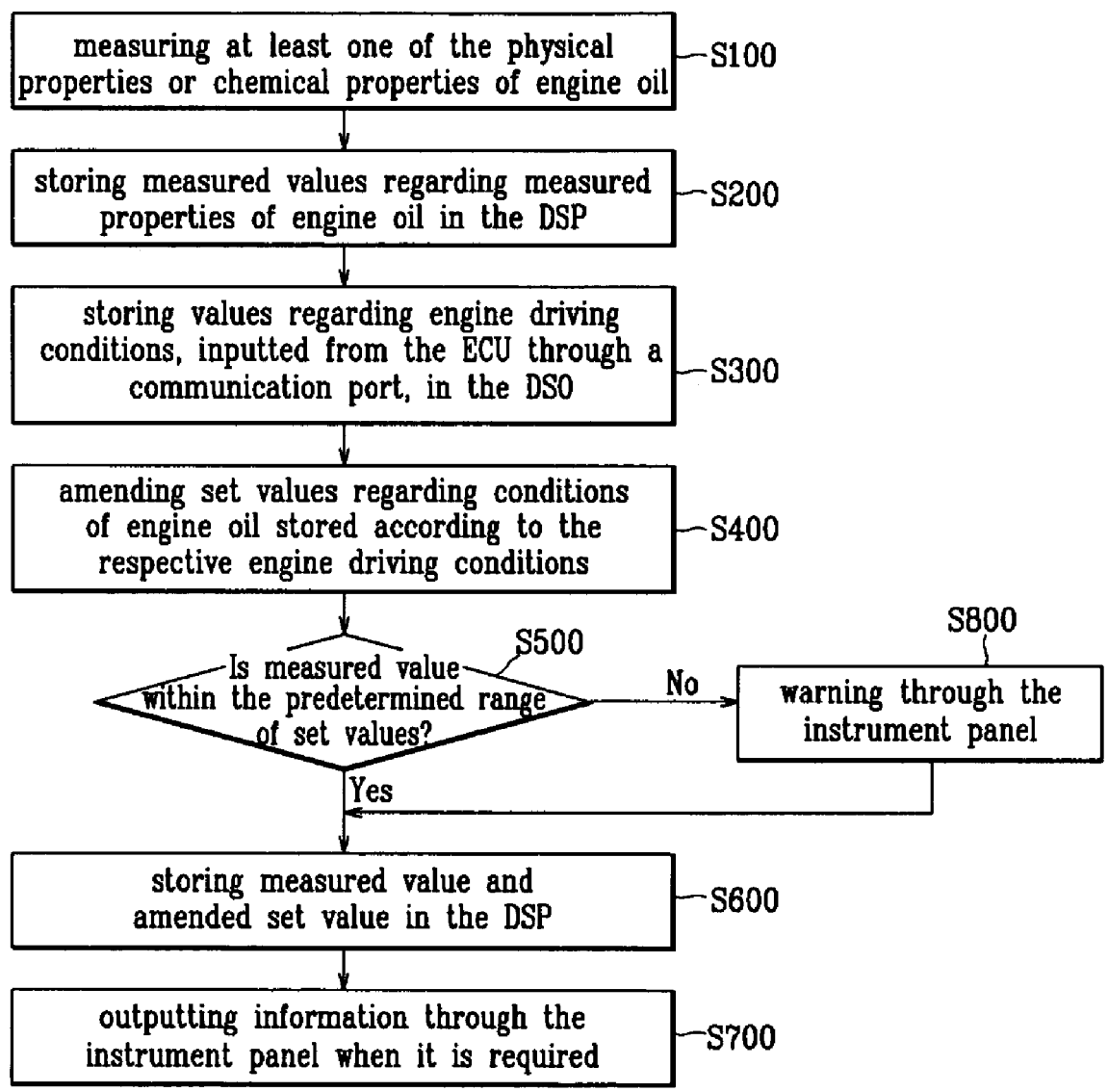
FIG. 7 is a flow chart illustrating a method for scanning engine oil according to an exemplary embodiment of the present invention.

FIG. 7 is flowchart to explain a method for scanning engine oil according to an exemplary embodiment of the present invention. A control portion including a DSP 20 is programmed to control the apparatus for scanning engine oil according to a process, as shown in the flow chart of FIG. 7.

Firstly, physical and/or chemical properties of engine oil are measured in step S100.

Here, the process of measuring physical properties of engine oil may include at least one process of measuring viscosity of engine oil with the oil viscosity sensor, measuring a level of engine oil with the oil level sensor, and measuring oil temperature with the oil temperature sensor.

In addition, the process of measuring chemical properties of engine oil may include a process of measuring a dielectric constant of engine oil with the oil oxidation degree sensor.

Measured values regarding the measured properties of the engine oil are inputted to the DSP in step S200.

Subsequently, information on engine driving conditions is measured by a driving condition measuring part installed in a vehicle, the measured information is inputted to the ECU, and then the information is inputted to the DSP from the ECU, in step S300.

Here, a process of measuring engine driving conditions may include at least one process of measuring driving speed of the vehicle with a vehicle speed sensor, measuring a quantity of intake air with an air flow sensor, and measuring engine rotation speed with a crank angle sensor.

Subsequently, one of set values (which were stored in advance) corresponding to the engine driving condition is selected, and the selected value is compared with the measured value regarding physical and/or chemical properties of engine oil, in step S500.

Set values of engine oil properties according to the engine driving conditions are stored in the DSP in advance. Therefore, when information on engine driving conditions is inputted, a corresponding set value of an oil property is selected. Then, the selected set value is compared with the measured value of the measured engine oil property.

In this step, it is determined whether the measured value of the engine oil property is in a range where a warning is required.

In other words, the DSP 20 compares the measured value of physical and chemical properties of engine oil measured by the complex sensor or respective sensors with the predetermined set value of the engine oil condition stored in advance.

After comparing the values, if the measured value regarding the measured properties of engine oil is out of the predetermined range stored in the DSP 20, the DSP 20 lights a warning lamp. However, if the measured value is within the predetermined range, the DSP 20 does not light the warning lamp.

Here, the set value, which is mapped in the DSP, may be amended according to the properties of engine oil or history of engine oil, in step S400.

That is, the DSP 20 may amend the mapped set value according to the driving condition measured by the ECU 30.

The amending may be performed such that a set value of oil viscosity is determined on the basis of at least one condition among the amount of change of oil temperature, the amount of change of engine rotation speed, the amount of change of mileage, the amount of change of intake air, and the amount of change of air at an idle state.

If the measured value is within a range of the set value, the measured value and the amended set value are stored in the DSP in step S600.

In addition, the measure value and a result of comparison are outputted through an output part in step S700.

The measured value, amended value, and value for optimum engine state of engine oil are stored in a flash memory 22 of the DSP 20, and the values are expressed through the output part such that the drivers or engineers can notice it.

Such an output part may be an instrument panel 40, and may be a monitor of a system scanner 50.

The values expressed by the system scanner 50 are a viscosity, a quantity, a pressure, a degree of oxidation, a degree of pollution, etc., of engine oil from a manufactured time to the present. Therefore, the driver and engineer can notice the electric current quality or state of the engine oil, and the history of the engine oil.

However, when a value of measured properties is out of the range in the step S500, the DSP warns of the same through the instrument panel 40, in step S800.

That is, the DSP 20 sends a signal for lighting an engine oil warning lamp.

According to the present exemplary embodiment of the present invention, the DSP 20 may be programmed to compare the quality of engine oil measured in an engine stop state with the quality of engine oil measured in the engine operation state. In this case, measured oil temperature oil_t is compared with a set limit temperature oil_t_low and oil_t_high, and measured engine rotation speed engine_rpm is compared with a set rotation speed limit rpm_low and rpm_high.

In particular, an average value of the values of properties of engine oil measured in the engine stop state and engine operation state may be calculated and may be used for scanning the quality of engine oil.

In addition, according to an exemplary embodiment of the present invention, a history of an engine operation cycle (from engine on to engine off) may be considered to scan the engine oil.

That is, when amending a value set in the flash memory of the DSP 20 in the step S400, the limit value of the viscosity of the engine oil may be amended on the basis of the accumulated number of engine rotations.

In addition, the limit value of the degree of the oxidation set in the DSP 20 may be amended on the basis of the accumulated number of engine rotations.

According to the present invention, the sensor is not deteriorated, due to the self-cleaning function, and durability is increased.

In addition, the optimum state of engine oil is noticed to a driver or an engineer. Therefore, instead of mere exchange timing of engine oil according to time duration, the optimum oil quality and optimum exchange timing according to various conditions is notified to the driver or an engineer.

In addition, there are advantages of determining whether the repair of a friction part is required and correctly evaluating a worth of a used car, in the case of repairing a vehicle or evaluating a used car, by enabling knowledge of the history of exchanging engine oil from a manufactured time to the present, engine oil dissipation rate based on the history, a viscosity, a degree of oxidation, and a deterioration rate based on the driving mileage.

In addition, according to the plurality of oil level electrodes divided into parts, rolling angle of the vehicle, pitching angle of the vehicle, etc., can be achieved on the basis of engine oil level measured at each of the oil level electrodes for stability control.

In addition, according to the plurality of oil level electrodes divided into parts, the amount of engine oil can be measured on the basis of the engine oil levels measured at each of the oil level electrodes.

Since the oil viscosity sensor includes a ring-shaped piezoelectric element, a vibration shaft penetrating the piezoelectric element, and a vibration tube, durability of the sensor can be improved.

In addition, since the vibration tube and the lower surface of the probe is contacted with engine oil, and the area contacted with engine oil for sensing is enlarged, a ratio of signal/noise is improved.

In addition, measuring accuracy is improved and the measuring error is reduced when the viscosity sensor has a structure including a pipe-shaped piezoelectric element, two inside electrodes separately mounted to the interior circumference of the piezoelectric element, and an outside electrode mounted to the exterior circumference of the piezoelectric element, and one part is exposed to the engine oil and the other part is exposed to the air.

In addition, although a secular change occurs, an effect of amending absolute viscosity can be achieved by determining relative viscosity, In addition, since a piezoelectric element has a shape of a pipe, a contact area with engine oil is enlarged and accuracy of the measurement can be improved.

In addition, since a plurality of ring-shaped piezoelectric elements are stacked, vibration can be increased.

In addition, since the case of the complex sensor has a shape of an inverted "L" (⌐) and is mounted to the side wall of an oil pan, the complex sensor can be more stable against external impact.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. An apparatus for scanning states of engine oil, comprising:
    an oil property measuring part for measuring physical and chemical properties of engine oil;
    a driving condition measuring part for measuring an engine driving condition;
    a control portion where conditions of engine oil corresponding to engine driving conditions are stored as set values, for selecting a set value for a state of engine oil corresponding to the measured engine driving condition, and calculating a result value regarding a quality of engine oil on the basis of comparison of a measured value for the state of engine oil inputted from the driving condition measuring part and the set value; and
    an output part for outputting a predetermined output depending on the result value;
    wherein the oil property measuring part is a complex sensor comprising:
        a cylindrical case having a hollow space therein;
        an oil level sensor, an oil oxidation degree sensor, an oil viscosity sensor, and an oil temperature sensor installed in the case; and
        a DSP for calculating values for physical and chemical properties of engine oil, on the basis of values measured by each of the sensors, wherein
        the oil level sensor comprises
            an input electrode having a shape of a pipe, installed in the case, and formed such that an electric current can be applied thereto, and
            an oil level electrode having a shape of a pipe, disposed apart from an inner surface of the input electrode, and formed to receive an electric current from the input electrode,
        the oil oxidation degree sensor comprises
            the input electrode, and
            an oil oxidation degree electrode having a shape of a pipe, disposed at a lower portion of the oil level electrode, and formed to receive an electric current applied from the input electrode,
        the oil viscosity sensor comprises
            a piezoelectric element and a metal membrane covering the piezoelectric element, and
        the oil temperature sensor is mounted to the case.

2. The apparatus of claim 1, wherein the output part is an instrument panel or a system scanner.

3. The apparatus of claim 1, wherein the piezoelectric element of the oil viscosity sensor has a self-cleaning function by vibrating engine oil when the electric current is applied.

4. The apparatus of claim 1, wherein an oil hole through which the engine oil passes is formed at the case and the input electrode.

5. The apparatus of claim 1, wherein the oil viscosity sensor is mounted to the inside of the oil oxidation degree electrode by an O-ring made of rubber.

6. The apparatus of claim 1, wherein the DSP comprises
    an input/output port for receiving information by communicating with the oil property measuring part, an ECU, and the output part, and outputting a control signal;
    a CPU for calculating a quality of engine oil on the basis of a measured value inputted through the input/output port and information of the engine driving condition inputted from the ECU;

a flash memory for storing history of the condition of engine oil calculated by the CPU in a sequence of time; and a ROM for storing a program for operating the CPU.

7. An apparatus for scanning states of engine oil, comprising:

an oil property measuring part for measuring physical and chemical properties of engine oil;

a driving condition measuring part for measuring an engine driving condition;

a control portion where conditions of engine oil corresponding to engine driving conditions are stored as set values, for selecting a set value for a state of engine oil corresponding to the measured engine driving condition, and calculating a result value regarding a quality of engine oil on the basis of comparison of a measured value for the state of engine oil inputted from the driving condition measuring part and the set value; and an output part for outputting a predetermined output depending on the result value;

wherein the oil property measuring part includes at least one of an oil viscosity sensor, an oil level sensor, an oil temperature sensor, and an oil oxidation degree sensor; and wherein the oil viscosity sensor comprises:

a viscosity sensor case;

a pipe-shaped piezoelectric element;

an inside electrode mounted to the inner surface of the piezoelectric element and vertically separated therefrom;

an outside electrode mounted to the exterior surface of the piezoelectric element; and a plurality of electric wires for supplying electric power to an inside electrode, wherein one part of the piezoelectric element with the outside electrode is exposed to the engine oil and the other part of the piezoelectric element with the outside electrode is exposed to air, and when an electric current is applied, the two parts of the piezoelectric element are torsionally vibrated in opposite directions to each other, and the control portion calculates a relative viscosity of engine oil on the basis of a measured damping force of air and a measured damping force of engine oil.

8. The apparatus of claim 7, wherein the oil level sensor comprises:

an input electrode formed such that an electric current is applied thereto; and an oil level electrode disposed apart from the input electrode and formed to receive an electric current output from the input electrode, and the control portion calculates a capacitance and a dielectric constant of engine oil between the input electrode and the oil level electrode on the basis of the input current of the input electrode and the output current of the oil level electrode, and calculates an oil level on the basis of the calculated capacitance and dielectric constant of engine oil.

9. The apparatus of claim 8, wherein
the input electrode has a shape of a pipe, and
the oil level electrode has a shape of a pipe having a smaller diameter than the input electrode.

10. The apparatus of claim 9, wherein
the oil level electrode is divided into a plurality of parts, and
the control portion calculates a plurality of oil levels at the respective divided parts of the oil level electrode on the basis of signals of the output electric current of the oil level electrodes and the input electric current of the input electrode.

11. The apparatus of claim 10,
further comprising a supporting part for mounting the oil level electrode, wherein the supporting part is formed of an insulating material to have a shape of a pipe, and the oil level electrode is fixed to an exterior surface of the supporting part.

12. The apparatus of claim 11, wherein
four vertical protruded parts are formed along a longitudinal direction on an outer surface of the supporting part, and
the vertical protruded parts are disposed between two adjacent divided parts of the oil level electrode so as to insulate respective divided parts of the oil level electrode.

13. The apparatus of claim 7, wherein the oil oxidation degree sensor comprises:

an input electrode applying electric current; and an oil oxidation degree electrode disposed apart from the input electrode and formed to receive the electric current from the input electrode, and the control portion calculates a capacitance of engine oil between the input electrode and the oil oxidation degree electrode on the basis of the input electric current of the input electrode and the output electric current of the oil oxidation degree electrode, calculates a dielectric constant on the basis of the calculated capacitance, and calculates an oil level on the basis of the calculated capacitance and dielectric constant of engine oil.

14. The apparatus of claim 13, wherein
the input electrode has a shape of a pipe, and
the oil oxidation degree electrode has a shape of a pipe having a smaller diameter than the input electrode.

15. The apparatus of claim 7, wherein
an inner surface of the viscosity sensor case is projected inward,
a longitudinal center of the outside electrode is fixedly mounted to the projected part of the inner surface of the viscosity sensor case, and
the inside electrode is vertically separated at a position corresponding to a fixing position of the outside electrode to the viscosity sensor case.

16. The apparatus of claim 15, wherein the piezoelectric element of the oil oxidation degree sensor has a self-cleaning function by vibrating engine oil when the electric current is applied.

* * * * *